United States Patent
Weston

(10) Patent No.: US 7,753,927 B2
(45) Date of Patent: Jul. 13, 2010

(54) CORNEAL PUNCH

(76) Inventor: Philip Douglas Weston, 3 Townend Cottages, Grantley, North Yorkshire (GB) HG4 3PJ ( * ) Notice: Subject to any disclaimer, the term of this patent is extended or adjusted under 35 U.S.C. 154(b) by 1330 days.

(21) Appl. No.: 10/173,131

(22) Filed: Jun. 17, 2002

(65) Prior Publication Data

US 2003/0060838 A1 Mar. 27, 2003

Related U.S. Application Data

(60) Provisional application No. 60/298,717, filed on Jun. 15, 2001.

(51) Int. Cl.
*A61F 9/00* (2006.01)
*A61F 9/01* (2006.01)
*A61F 9/011* (2006.01)

(52) U.S. Cl. ............... 606/166; 606/167; 606/171; 606/180

(58) Field of Classification Search .......... 606/166, 606/167, 184, 185, 171, 180

See application file for complete search history.

(56) References Cited

U.S. PATENT DOCUMENTS

| 4,205,682 A * | 6/1980 | Crock et al. ............... 606/166 |
| 4,236,519 A | 12/1980 | La Russa et al. |
| 4,319,575 A * | 3/1982 | Bonte ........................ 606/166 |
| 4,336,805 A * | 6/1982 | Smirmaul ................. 606/166 |
| 4,718,420 A * | 1/1988 | Lemp ........................ 606/166 |
| 4,796,623 A * | 1/1989 | Krasner et al. ............. 606/166 |
| 5,011,498 A | 4/1991 | Krumeich et al. |
| 5,312,428 A * | 5/1994 | Lieberman ................. 606/166 |
| 5,334,213 A | 8/1994 | Price, Jr. |
| 5,464,417 A * | 11/1995 | Eick .......................... 606/166 |
| 5,649,944 A * | 7/1997 | Collins ..................... 606/166 |

* cited by examiner

*Primary Examiner*—Anhtuan T Nguyen
*Assistant Examiner*—Amy T Lang
(74) *Attorney, Agent, or Firm*—Ira S. Dorman

(57) ABSTRACT

A corneal punch comprising a base unit having a first annular mating surface surrounding a well in which a donor cornea may be located, and a separate guide unit including an inner annular guide shaft and an outer locating ring connected to the guide shaft and having a second annular mating surface. The base unit and the guide unit may be releasably positioned in registration with each other by way of the first and second mating surfaces such that the guide shaft is substantially coaxial with the well.

14 Claims, 3 Drawing Sheets

CORNEAL PUNCH

CROSS-REFERENCE TO RELATED APPLICATIONS

This application claims priority of my U.S. Provisional patent Application No. 60/298,717, filed 15 Jun. 2001, and incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a corneal punch for cutting corneal grafts from donor corneas prior to transplantation of the grafts to patients with damaged or diseased corneas.

2. General Background of the Invention

In the field of eye surgery, it is sometimes necessary to perform a corneal transplant by replacing a diseased or damaged cornea of a patient with a donor cornea harvested from an immunologically compatible cadaver. This is generally achieved by removing at least a central portion of the diseased or damaged cornea from a patient's eye using a trephine, using a corneal punch to cut an equivalent portion from a donor cornea (this portion being known in the art as a donor graft), and then inserting the donor graft into the space on the surface of the patient's eye left vacant by removal of the diseased or damaged portion of the patient's original cornea.

A known corneal punch comprises a base unit including a well in which a donor cornea may be located, and a guide unit which is then placed on top of the base unit and registered therewith by way of four pins provided on the underside of the guide unit and which locate into four corresponding holes provided on an upper peripheral surface of the base unit. The guide unit is a generally solid block of similar size to the base unit, and includes a central aperture which is located directly over the well of the base unit when the guide unit is in registration therewith. The central aperture is circular, and is sized and shaped so as slidably to receive a corneal trephine. The corneal trephine may be moved up and down within the guide unit in a reciprocating manner so as to allow a donor graft to be cleanly cut from the donor cornea.

This known corneal punch has two significant disadvantages. Firstly, it is difficult to register the guide unit with the base unit because the four pins are difficult to locate within the four holes. Secondly, because the guide unit is substantially solid and opaque, it is not possible for a surgeon or technician to have a clear view of the donor cornea when cutting the donor graft therefrom with a corneal trephine.

According to the present invention, there is provided a corneal punch comprising a base unit having a first annular mating surface surrounding a well in which a donor cornea may be located, and a separate guide unit including an inner annular guide shaft and an outer locating ring connected to the guide shaft and having a second annular mating surface, wherein the base unit and the guide unit may be releasably positioned in registration with each other by way of the first and second mating surfaces such that the guide shaft is substantially coaxial with the well.

Advantageously, the outer locating ring of the guide unit is connected to the guide shaft by way of one or more spokes or webs so as to provide one or more windows in the guide unit. The one or more windows allow the well to be observed when the guide unit is in registration with the base unit. Furthermore, a donor cornea or donor graft may be manipulated through the one or more windows when in the well, for example with a pointed tool or the like, for positioning or other purposes.

The one or more spokes or webs may be provided with corrugations or ridges or the like on upper surfaces thereof so as to provide a good gripping surface for a person's fingers when pushing down on the guide unit so as to ensure it is held firmly in place on the base unit when the corneal punch is in an assembled condition. Alternatively or in addition, the inner annular guide shaft of the guide unit may be provided with peripheral ridges or corrugations, such as a knurled outer edge, for providing a finger grip.

Alternatively, the guide unit or at least a part thereof, preferably a part between the locating ring and the guide shaft, may be made out of a substantially transparent material so as to allow the well to be observed when the guide unit is in registration with the base unit.

In this way, the present invention provides a corneal punch where it is relatively easy to position the guide unit in registration with the base unit, in which the well is visible to a surgeon or technician when the guide unit is in place, and in which access to a donor cornea or donor graft is provided through one or more windows so as to allow the cornea or graft to be manipulated or repositioned when in the well.

The first and second mating surfaces may comprise annular mating flanges and shoulders so as to provide good registration between the base unit and guide unit. The annular mating flange of the first mating surface may fit inside the annular mating flange of the second surface, or vice versa.

The guide shaft is sized and shaped so as slidably and snugly to receive an annular corneal trephine, and to allow a cutting edge of the trephine to be lowered into the well so as to cut a donor graft from a donor cornea located therein.

The base unit may be provided with peripheral finger grips or the like so as to allow it to be held firmly in position on a flat surface when cutting a donor graft from a donor cornea. The finger grips may take the form of corrugations or ridges or the like formed on a surface of the base unit. In some embodiments, the base unit includes a generally planar base plate which allows the corneal punch to be held down on a flat surface in a secure manner. The base plate may include a generally annular cut-out portion in which a corneal trephine may be snugly located for storage purposes.

In preferred embodiments, the present invention is made out of surgical grade stainless steel, although other materials such as plastics or polymers or other metals may be used where appropriate. The guide unit in particular may be made fully or partially out of a substantially transparent plastics material so as to allow the well in the base unit to be observed when the guide unit is in position.

It is preferred that the present invention is a disposable corneal punch, in that it is discarded after use. However, certain embodiments may be sterilised, for example in an autoclave, and then used again.

The well may comprise a generally circular concave dish sunk into a central part of the base unit and adapted to contain a donor cornea.

BRIEF DESCRIPTION OF THE SEVERAL VIEWS OF THE DRAWINGS

For a better understanding of the present invention and to show how it may be carried into effect, reference shall now be made by way of example to the accompanying drawings, in which.

DETAILED DESCRIPTION OF THE INVENTION

Figure 1:
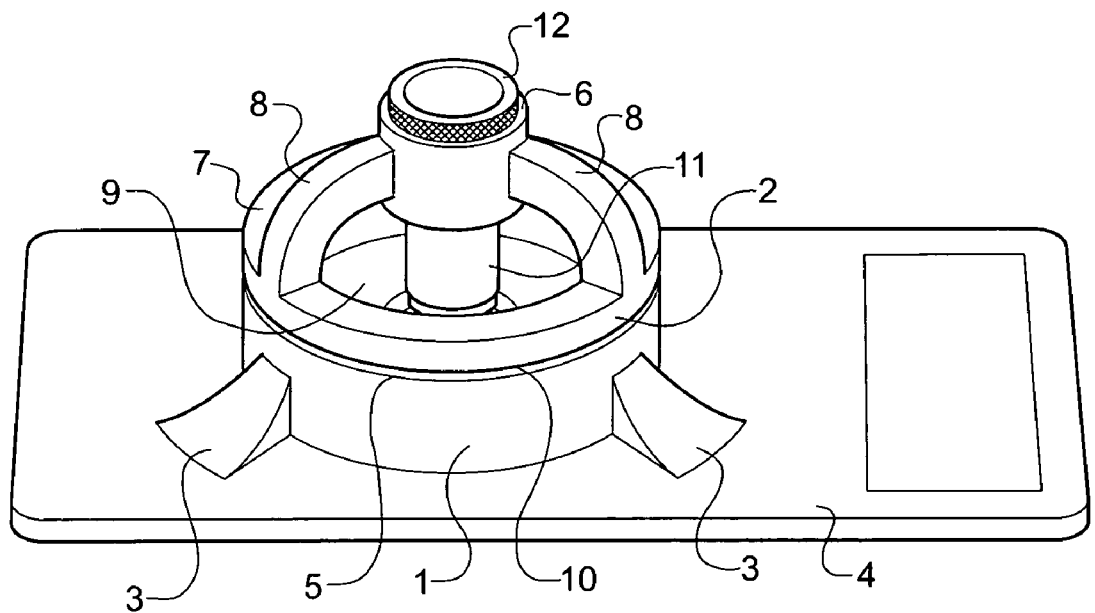
FIG. 1 shows a first embodiment of the present invention fitted with a corneal trephine.

FIG. 1 shows a corneal punch comprising a base unit 1 and a guide unit 2 located in registration therewith. The base unit 1 includes peripheral finger grips 3 and is mounted on a plate 4 so as to allow it to be held steady on a flat surface. The base unit 1 is generally cylindrical in shape, and includes an internal central well 13 (see FIG. 3) which is in the form of a generally circular concave dish adapted to support a donor cornea. An annular mating surface 5 is provided at the top of the base unit 1, the well 13 being coaxial with the annular mating surface 5. The guide unit 2 has an inner annular guide shaft 6 connected to an outer locating ring 7 by way of three spokes 8, with windows 9 being defined between the spokes 8. The outer locating ring 7 is provided with a mating surface 10 at its base, the mating surface 10 being shaped so as to co-operate with the mating surface 5 of the base unit 1 and to hold both the base unit 1 and the guide unit 2 in registration with each other. It will be appreciated that the provision of two annular mating surfaces 5, 10 allows the guide unit 2 to be easily placed on top of the base unit 1 in registration therewith. The guide shaft 6 is substantially coaxial with the outer locating ring 7, the annular mating surface 5, 10 and the well 13 when the guide unit 2 is placed in registration on the base unit 1. The guide shaft 6 is sized and shaped so as slidably and snugly to receive a corneal trephine 11 having a knurled ring 12 at its upper end and an annular blade 18 (see FIG. 3) at its lower end. The annular blade 18 of the corneal trephine 11 may thus be controllably lowered onto a donor cornea located within the well 13 so as to cut a donor graft therefrom, with the windows 9 providing a view into the well 13. Both the trephine 11 and the guide unit 2 may be rotated relative to the base unit 1 when in registration therewith so as to aid the cutting process.

Figure 2:
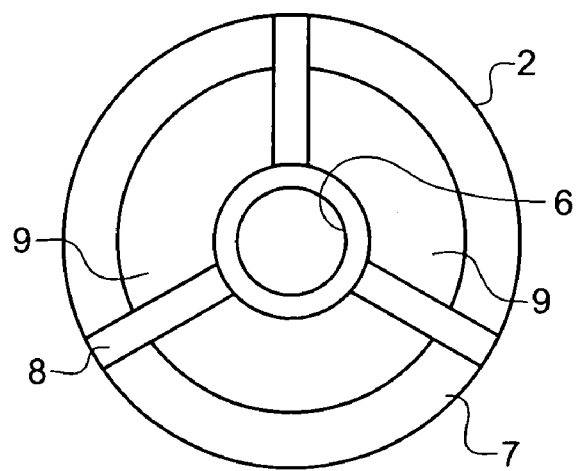
FIG. 2 shows a plan view of a guide unit of the first embodiment of the present invention.

FIG. 2 shows a plan view of the guide unit 2 when separated from the base unit 1, the guide unit 2 incorporating the guide shaft 6, the spokes 8, the windows 9 and the outer locating ring 7.

Figure 3:
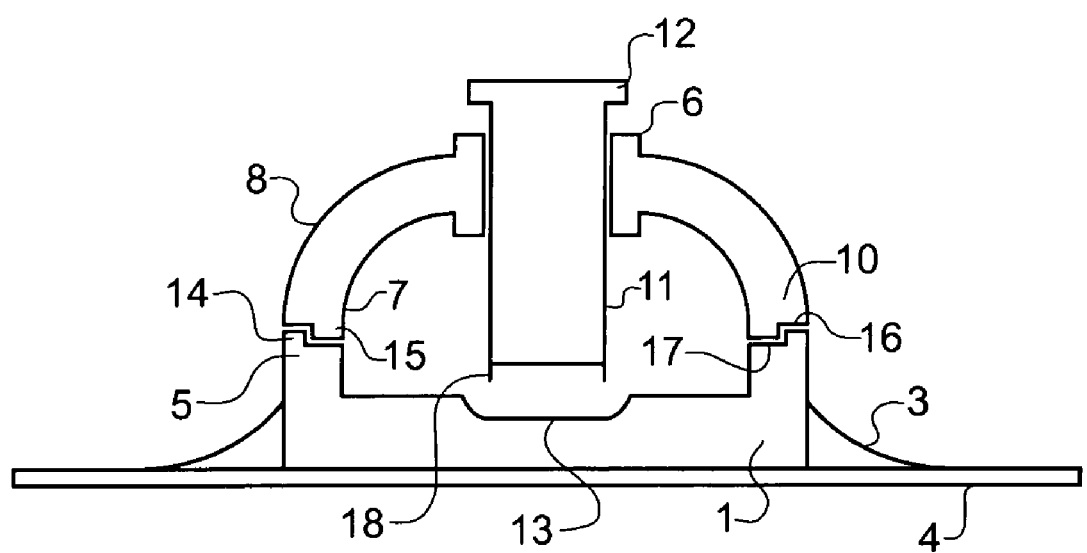
FIG. 3 shows a section through the embodiment of FIG. 1.

FIG. 3 shows a cross section through the embodiment of FIG. 1, including the base unit 1, the guide unit 2, the finger grips 3 and the plate 4 and the internal central well 13. The annular mating surface 5 of the base unit 1 is shown in registration with the mating surface 10 of the outer locating ring 7 of the guide unit 2. The mating surfaces 5, 10 are shown as stepped surfaces comprising complementary mating flanges 14, 15 and shoulders 16, 17, although it will be apparent that any other suitable mating surfaces may be used, provided that they serve to hold the base unit 1 and the guide unit 2 in registration with each other. The annular guide shaft 6 of the guide unit 2 is shown connected to the outer locating ring by way of spokes 8. A corneal trephine 11 having a knurled ring 12 at its upper end and an annular blade 18 at its lower end is positioned slidably and snugly in the guide shaft 6, and may be lowered so that the annular blade 18 may cut a donor graft from a donor cornea in the well 13.

Figure 4:
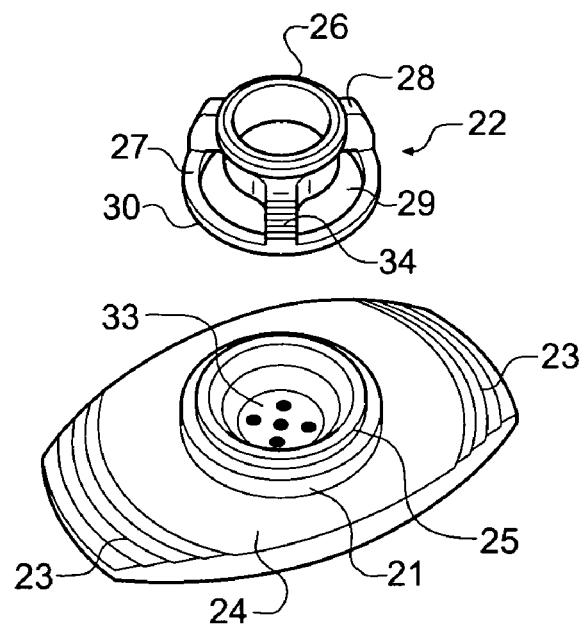
FIG. 4 shows a perspective exploded view of a second embodiment of the present invention.
Figure 5:
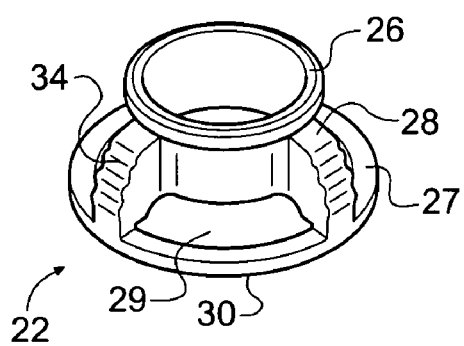
FIG. 5 shows a detail of a guide unit of the embodiment of FIG. 4.

FIGS. 4 and 5 show an alternative corneal punch comprising a base unit 21 and a guide unit 22 which may be located in registration therewith. The base unit 21 includes a base plate 24 having finger grips 23 so as to allow it to be held steady on a flat surface. The base unit 21 has a generally cylindrical central portion, and includes an internal central well 33 which is in the form of a generally circular concave dish adapted to support a donor cornea. An annular mating surface 25 is provided at the top of the base unit 21, the well 33 being coaxial with the annular mating surface 25. The guide unit 22 has an inner annular guide shaft 26 connected to an outer locating ring 27 by way of three spokes 28, with windows 29 being defined between the spokes 28. Upper edges of the spokes 28 are provided with finger grips 34 in the form of corrugations or ridges. The outer locating ring 27 is provided with a mating surface 30 at its base, the mating surface 30 being shaped so as to co-operate with the mating surface 25 of the base unit 21 and to hold both the base unit 21 and the guide unit 22 in registration with each other. It will be appreciated that the provision of two annular mating surfaces 25, 30 allows the guide unit 22 to be easily placed on top of the base unit 21 in registration therewith. The guide shaft 26 is substantially coaxial with the outer locating ring 27, the annular mating surface 25, 30 and the well 33 when the guide unit 22 is placed in registration on the base unit 21. The guide shaft 26 is sized and shaped so as slidably and snugly to receive a corneal trephine.

Figure 6:
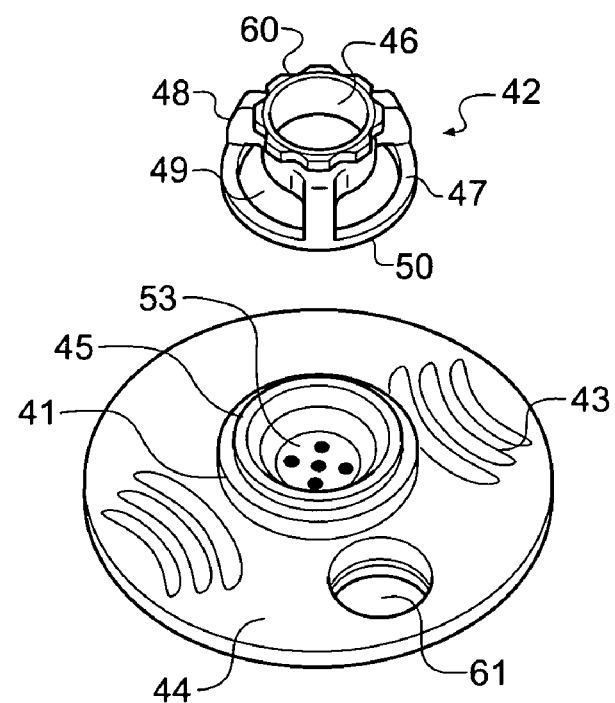
FIG. 6 shows a perspective exploded view of a third embodiment of the present invention.

FIG. 6 shows a further alternative corneal punch comprising a base unit 41 and a guide unit 42 which may be located in registration therewith. The base unit 41 includes a circular base plate 44 having finger grips 43 so as to allow it to be held steady on a flat surface. The base unit 41 has a generally cylindrical central portion, and includes an internal central well 53 which is in the form of a generally circular concave dish adapted to support a donor cornea. An annular mating surface 45 is provided at the top of the base unit 41, the well 53 being coaxial with the annular mating surface 45. The guide unit 42 has an inner annular guide shaft 46 connected to an outer locating ring 47 by way of three spokes 48, with windows 49 being defined between the spokes 48. An outer edge of the inner annular guide shaft 46 is formed as a knurled ring 60 so as to provide a good grip for a user of the corneal punch. The outer locating ring 47 is provided with a mating surface 50 at its base, the mating surface 50 being shaped so as to co-operate with the mating surface 45 of the base unit 41 and to hold both the base unit 41 and the guide unit 42 in registration with each other. It will be appreciated that the provision of two annular mating surfaces 45, 50 allows the guide unit 42 to be easily placed on top of the base unit 41 in registration therewith. The guide shaft 46 is substantially coaxial with the outer locating ring 47, the annular mating surface 45, 50 and the well 53 when the guide unit 42 is placed in registration on the base unit 41. The guide shaft 46 is sized and shaped so as slidably and snugly to receive a corneal trephine. Furthermore, the base plate 44 is provided with a cut-out portion 61 sized and shaped so as snugly to hold at least a portion of a corneal trephine (not shown) for storage purposes.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. Manually operated corneal punch apparatus comprising:
   a base unit having a lower portion with means for defining, on a normally vertical axis, an upwardly opening well for the receipt of a donor cornea, and a sidewall portion comprising a first annular mating surface surrounding said well;
   a separate guide unit dismountably mounted on said base unit and comprised of an inner guide shaft having a cylindrical interior surface, an outer locating ring comprising a second annular mating surface, and one or more spokes or webs rigidly joining said guide shaft to said locating ring with said locating ring concentrically disposed radially outwardly of said guide shaft and with said interior surface of said guide shaft, and said first and second annular mating surfaces, coaxially aligned on said vertical axis, said first and second annular mating surfaces being dimensioned and configured for mated, direct interengagement with one another and to enable rotation about the vertical axis of said guide unit relative to said base unit when said first and second annular mating surfaces are in direct engagement and when the guide unit and base unit are in registration therewith to aid the cutting process; and a corneal trephine member having a generally cylindrical portion snugly engaged within said shaft of said guide unit and dimensioned and configured for manual axial sliding movement, and manual rotation, on said vertical axis, said trephine member having means for mounting a circular cutting blade coaxially on a lower end portion thereof.

2. The corneal punch apparatus of claim 1, wherein at least one of the one or more spokes or webs is provided with corrugations or ridges which each serve as a finger grip.

3. The corneal punch apparatus of claim 1, wherein at least a part of the guide unit is made out of a substantially transparent material through which the well may be observed.

4. The corneal punch apparatus of claim 1, wherein the first and second mating surfaces comprise complementary annular mating flanges and shoulders.

5. The corneal punch apparatus of claim 1, wherein the base unit is provided with peripheral finger grips or the like so as to allow it to be held firmly in place on a surface.

6. The corneal punch apparatus of claim 1, wherein the well comprises a generally circular concave dish.

7. The corneal punch apparatus of claim 1, wherein the base unit includes a generally planar base plate.

8. The corneal punch apparatus of claim 7, wherein the base plate includes a cut-out portion sized and shaped so as to hold at least a portion of a corneal trephine for storage purposes.

9. The corneal punch apparatus of claim 1, wherein the one or more spokes or webs of said guide unit are disposed radially outwardly of said vertical axis and define one or more windows that provide physical access to the well from an exterior of the corneal punch apparatus.

10. The corneal punch apparatus of claim 9, wherein the one or more windows are sized and positioned so as to allow manipulation or repositioning of the donor cornea with a tool from outside the corneal punch apparatus when the donor cornea is located in the well.

11. A method for cutting a disc from a donor cornea, comprising the steps:

providing a manually operated corneal punch apparatus comprising:

a base unit having a lower portion with means for defining, on a normally vertical axis, an upwardly opening well for the receipt of a donor cornea, and a sidewall portion comprising a first annular mating surface surrounding said well;

a separate guide unit mountable on said base unit and comprised of an inner guide shaft having a cylindrical interior surface, an outer locating ring comprising a second annular mating surface, and one or more spokes or webs rigidly joining said guide shaft to said locating ring with said locating ring concentrically disposed radially outwardly of said guide shaft and, when said guide unit is mounted on said base unit, with said interior surface of said guide shaft and said first and second annular mating surfaces coaxially aligned on said vertical axis, said first and second annular mating surfaces being dimensioned and configured for mated, direct interengagement with one another and for rotation about the vertical axis of said guide unit relative to said base unit when said first and second annular mating surfaces are in direct engagement and when the guide unit and base unit are in registration therewith to aid the cutting process; and a corneal trephine member having a generally cylindrical portion snugly engaged within said shaft of said guide unit and dimensioned and configured for manual axial sliding movement, and manual rotation, on said vertical axis when said guide unit is mounted on said base unit, said trephine member having means for mounting a circular cutting blade coaxially on a lower end portion thereof;

mounting a circular cutting blade coaxially on a lower end portion of said trephine member;

placing a donor cornea in said well of said lower wall structure, with said guide unit dismounted from said base unit;

thereafter mounting said guide unit upon said base unit; and effecting cutting of said donor cornea by manually moving said trephine member into contact with said donor cornea, and manually rotating at least said trephine member while in contact with said donor cornea, so as to cause said cutting blade to cut said donor cornea and thereby enable the removal of a donor graft disc therefrom.

12. The method of claim 11 wherein the one or more spokes or webs of the guide unit define one or more windows through which the well may be observed, and wherein the donor cornea is manipulated or repositioned in the well by way of a tool that is inserted through at least one of the windows, of the mounted guide unit, from outside the corneal punch apparatus.

13. The method of claim 11 wherein, in said step of effecting cutting, said guide unit is also manually rotated relative to said base unit.

14. The method of claim 11 further including the additional step of inserting the removed donor graft disc into a receptor eye, said method being a method for performing corneal surgery.

* * * * *